United States Patent
Aho et al.

(10) Patent No.: US 9,079,010 B2
(45) Date of Patent: *Jul. 14, 2015

(54) TRANSCRANIAL MAGNETIC STIMULATION INDUCTION COIL DEVICE WITH ATTACHMENT PORTION FOR RECEIVING TRACKING DEVICE

(75) Inventors: Matti Aho, Nummela (FI); Henri Hannula, Helsinki (FI)

(73) Assignee: Nexstim Oy, Helsinki (FI)

( * ) Notice: Subject to any disclaimer, the term of this patent is extended or adjusted under 35 U.S.C. 154(b) by 482 days.

This patent is subject to a terminal disclaimer.

(21) Appl. No.: 12/944,768

(22) Filed: Nov. 12, 2010

(65) Prior Publication Data

US 2011/0060179 A1    Mar. 10, 2011

Related U.S. Application Data

(63) Continuation-in-part of application No. 11/847,544, filed on Aug. 30, 2007, now Pat. No. 7,854,232.

(60) Provisional application No. 60/823,966, filed on Aug. 30, 2006.

(51) Int. Cl.
*A61N 2/02* (2006.01)
*A61N 1/08* (2006.01)
*A61N 2/00* (2006.01)

(52) U.S. Cl.
CPC ... *A61N 2/02* (2013.01); *A61N 1/08* (2013.01); *A61N 2/006* (2013.01)

(58) Field of Classification Search
CPC ................... A61B 19/5244; A61N 2/00–2/12
USPC ............... 600/9–15, 407, 425–426; 606/130; 250/203.1
See application file for complete search history.

(56) References Cited

U.S. PATENT DOCUMENTS

| | | | |
|---|---|---|---|
| 5,834,759 A * | 11/1998 | Glossop | 250/203.1 |
| 5,921,992 A * | 7/1999 | Costales et al. | 606/130 |
| 6,351,659 B1 | 2/2002 | Vilsmeier | |
| 6,503,187 B1 | 1/2003 | Ilmoniemi et al. | |
| 6,830,544 B2 | 12/2004 | Tanner | |
| 6,926,660 B2 | 8/2005 | Miller | |
| 7,043,961 B2 | 5/2006 | Pandey et al. | |
| 2003/0181918 A1* | 9/2003 | Smothers et al. | 606/86 |
| 2004/0267242 A1* | 12/2004 | Grimm et al. | 606/1 |
| 2005/0033380 A1 | 2/2005 | Tanner et al. | |
| 2005/0075560 A1 | 4/2005 | Hannula et al. | |
| 2005/0215888 A1 | 9/2005 | Grimm et al. | |

OTHER PUBLICATIONS

Ettinger G et al. Experimentation with a transcranial magnetic stimulation system for functional brain mapping. Medical Image Analysis 2 (2) p. 133-142, 1998.*

* cited by examiner

*Primary Examiner* — Catherine B Kuhlman
(74) *Attorney, Agent, or Firm* — Seppo Laine Oy

(57) ABSTRACT

A transcranial magnetic stimulation induction coil device having a tracking device with a mating portion and at least one set of two or more reflective elements, a casing separate from a tracking device and containing at least one coil winding having a known orientation within the casing, and an attachment portion corresponding to the mating portion for removably attaching the tracking device to the casing such that, when attached, the reflective elements have a known orientation with respect to the known orientation of the coil winding.

12 Claims, 4 Drawing Sheets

TRANSCRANIAL MAGNETIC STIMULATION INDUCTION COIL DEVICE WITH ATTACHMENT PORTION FOR RECEIVING TRACKING DEVICE

CROSS REFERENCE TO RELATED APPLICATION

This application is a Continuation in Part of U.S. application Ser. No. 11/847,544 filed on Aug. 30, 2007 which claims priority from U.S. Provisional Application No. 60/823,966 filed Aug. 30, 2006, both of which are assigned to the assignee of this application and incorporated by reference herein.

FIELD OF THE INVENTION

The present invention relates generally to transcranial magnetic stimulation and, mare particularly, attachment of a tracking device to a transcranial magnetic stimulation ("TMS") induction coil device for use in tracking the location of the TMS coil device in relation to a subject's head.

BACKGROUND OF THE INVENTION

Transcranial magnetic stimulation ("TMS") uses an induction coil to induce an electric field ("E-field") within the brain. The locations of the brain exposed to a strong enough E-field will became activated, or stimulated. In navigated brain stimulation ("NBS"), the E-field induced in the brain by a TMS induction coil device is graphically represented on a display. As part of NBS, a three-dimensional ("3D") localization system is used to locate the TMS coil device accurately with respect to a subject's head. The localization system correlates TMS coil device location information with anatomical information representative of a subject's brain, which typically is obtained from magnetic resonance imaging ("MRI") of the brain. The E-field information is shown as an overlay on a graphical display of the subject's brain generated from the MRI images of the brain. By viewing the display, the user can interactively position the TMS coil device, in real time, in relation to the brain to stimulate a desired location of the brain.

A TMS induction coil device typically includes coils having 5 to 30 loops (windings) of capper wire located in a casing. The windings are normally circularly shaped or in the form of a figure 8. The shape, and the location of the maximum, of the E-field induced in the brain depend on the exact shape of the coil windings within the TMS coil device and their location and orientation with respect to the brain. In NBS, the strength and location of the E-field induced in the brain by the TMS coil device is determined from information representative of the location and orientation of the casing of the TMS coil device in relation to the brain and the location and orientation of the coil windings within and in relation to, respectively, the casing. The location and orientation of the casing is obtained from a navigation or tracking device, such as an infrared tracking device including an infrared transceiver and infrared reflective elements attached to the TMS coil device, that tracks the movement of the casing, as is conventional in the art. The location and orientation of the coil windings within the casing are determined by generating a model of the coil windings within the casing of the TMS coil device using information obtained from, for example, X-ray images of the casing of the TMS coil device.

It is known that, in NBS, navigation accuracy and the accuracy of the determination of the E-field induced in the brain are greatly affected by any inaccuracies associated with the tracking of the location of the coil windings within the TMS coil device with respect to the brain. Current prior art TMS coil devices, however, do not provide that a tracking device, such as, for example, a tracking device including three infrared reflective elements positioned at a predetermined orientation and spacing with respect to one another as is conventional in the art, is at a predetermined location and orientation or rotation angle on the casing of the TMS coil device each time that the tracking device is attached to the TMS coil device, such that the location and orientation of the reflective elements in relation to the casing are fixed.

For example, current TMS coil devices do not include a firm and solid coupling structure to which a tracking device can be attached conveniently and with ease, and where the coupling structure would substantially maintain its shape even after the tracking device has been repeatedly attached to and detached from the coupling structure. In the prior art, a tracking device is typically attached to a handle extending from the casing of a TMS coil device. The handle usually is a round, tubular plastic part having a relatively thin wall thickness. The rounded shape of the handle permits the tracking device to rotate easily about the handle, should a clamp securing the tracking device to the handle loosen even slightly. Further, based on the thin wall thickness of the handle, an originally round handle of a TMS coil device has been known to flatten slightly after repeated attachment and detachment of the tracking device.

Thus, the construction and configuration of handles of prior art TMS coil devices which the tracking device is attached to and detached from do not provide that the tracking device can be repeatedly attached to the TMS coil device at the same location and orientation in relation to the casing of the TMS coil device, and consequently to the coil windings in the casing. Each time that a tracking device is attached to a handle of a prior art TMS coil device, or sometimes following prolonged use of the TMS coil device with the tracking device attached thereto, a calibration must be performed to determine the location and orientation of the reflective elements of the tracking device in relation to the casing, and thus to the coil windings contained in the casing. The need for repeated calibration of the tracking device is undesirable. Furthermore, the possibility that the tracking device does not remain calibrated with respect to the casing, following an initial calibration when the tracking device is attached, can cause inaccuracies in the representation of the position and orientation of the casing in relation to the brain, and thus inaccuracies in the position of the E-field induced on the brain represented on a display as part of NBS performed with the TMS coil device, which are not known to the user during use of the TMS coil device.

Further, prior art TMS coil devices are ordinarily sold without any accompanying information that identifies locations on the casing of the TMS coil device which constitute fixed points of reference that can be used in connection with information obtained from a tracking device attached to the TMS coil device to accurately track movement of the TMS7 device in relation to the subject's head.

Therefore, there exists a need for a TMS coil device having an attachment portion which a tracking device can be repeatedly attached to and detached from with relative ease, and where, when the tracking device is attached to the attachment portion of the TMS coil device, the tracking device is at substantially the same, predetermined location and orientation in relation to the casing, and consequently the coil windings in the casing.

SUMMARY OF THE INVENTION

In accordance with the present invention, a TMS coil device includes a tracking device attachment portion having a configuration and size complementary to, and providing for precision mating and fixed attachment with, a mating attachment portion of a tracking device. Each time that the mating portion of the tracking device is fixedly mated to the tracking attachment portion of the TMS coil device, so as to attach the tracking device to the TMS coil device, the tracking device is at a predetermined location and orientation in relation to a casing of the TMS coil device.

In one embodiment of the invention, the casing of a TMS coil device includes the attachment portion, and the attachment portion and the mating portion are constructed to remain substantially structurally unchanged following repeated attachment of the tracking device to, and removal of the tracking device from, the TMS coil device.

In a further embodiment of the invention, the TMS coil device including the attachment portion has reflective material covering at least one location on an outer surface of the TMS coil device. The location defines a reference point that can be used to check the accuracy with which the tracking device is attached to the TMS coil device at an expected, predetermined location and orientation in relation to the TMS coil device. In one embodiment, an actual reference coordinate frame for the TMS coil device is generated based on the detected location of the reference point in relation to the detected location of a plurality of reflective elements of the tracking device attached to the TMS coil device, and the actual reference coordinate frame is compared to an expected, reference coordinate frame for the attached tracking device in relation to the TMS coil device. Based on any variance between the actual and expected reference coordinate frames, tracking device attachment calibration data for the TMS coil device with the attached tracking device, which is for use in performing NBS and based on the expected, reference coordinate frame, is suitably adjusted.

BRIEF DESCRIPTION OF THE DRAWINGS

Other objects and advantages of the present invention will be apparent from the following detailed description of the presently preferred embodiments, which description should be considered in conjunction with the accompanying drawings in which like references indicate similar elements and in which.

DETAILED DESCRIPTION OF THE INVENTION

The present invention of providing for precise attachment of a TMS coil device to a tracking device, such that the tracking device is at a predetermined position and orientation in relation to a casing of the TMS coil device containing coil windings each time that the tracking device is fixedly attached to the TMS coil device, is illustrated below in connection with a TMS coil device having a casing defining a recess for receiving and precisely mating with a complementarily configured mating attachment projection of a tracking device. It is to be understood, however, that any suitable coupling means known in the art for mating a first device with a second device, at precisely the same location and orientation in relation to the second device each time that the first device is fixedly mated to the second device, can be used in connection with the TMS coil device and the tracking device, respectively, so long as the coupling means are compatible for use in performing transcranial magnetic stimulation using the TMS coil device and the tracking device of interest.

Figure 1:
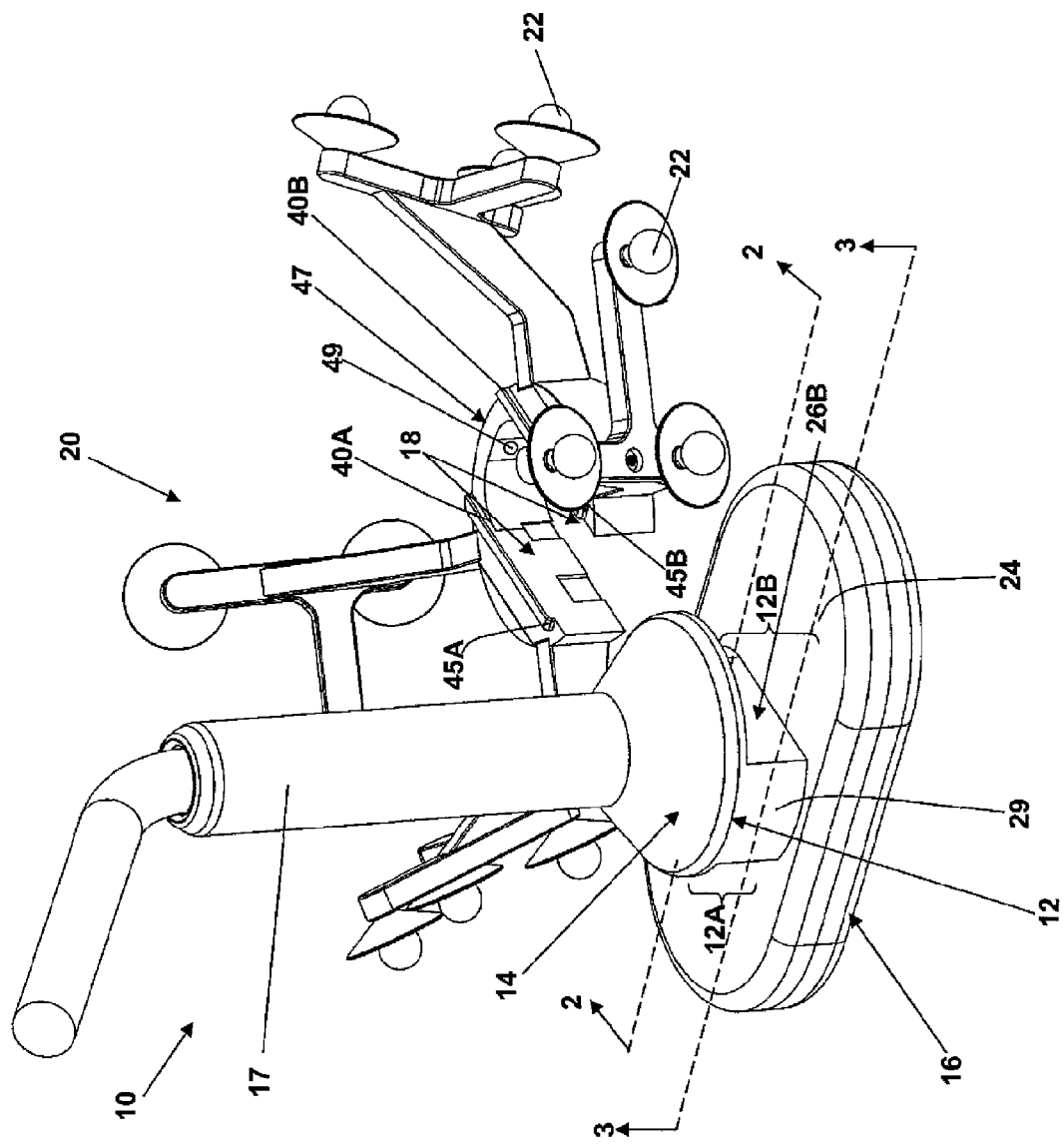
FIG. 1 is a side, perspective view of an exemplary TMS coil device including an attachment portion to which a mating portion of a tracking device can be coupled in accordance with the present invention.

FIG. 1 shows an exemplary embodiment of a TMS coil device 10 including a tracking device attachment portion 12, in accordance with the present invention, to which a tracking device can be repeatedly, precisely fixedly attached and then removed, and where each time that the tracking device is fixedly attached to the mating portion 12, the tracking device 20 is at a predetermined location and orientation in relation to the device 10, and in particular coil windings (not shown) contained in a casing 14 of the TMS coil device 10. Referring to FIG. 1, the casing 14 of the TMS coil device 10 includes a bottom portion 16, which contains the coil windings, and the attachment portion 12. The attachment portion 12 extends vertically away from a top outer surface 24 of the bottom portion 16 and connects to a handle 17 of the TMS coil device 10. The handle 17 of the TMS coil device 10 can be an integral portion of the casing or it can be a separate portion of the TMS coil device.

In a preferred embodiment, the coil windings have a predetermined size and shape and are positioned at a predetermined location within and orientation in relation to each other and the bottom portion 16, which also has a predetermined size and shape, as described in detail in TRANSCRANIAL MAGNETIC STIMULATION INDUCTION COIL DEVICE AND METHOD OF MANUFACTURE, U.S. patent application Ser. No. 11/847,511, filed Aug. 30, 2007, assigned to the assignee of this application and incorporated by reference herein ("TMS Coil Device Manufacture patent application"). The attachment portion 12 has a predetermined shape and size complementarily to the size and shape of a mating portion 18 of a tracking device 20. The tracking device 20 includes a plurality of infrared reflective elements 22 positioned at fixed, predetermined locations and orientations in relation to one another, as is conventional and well known in the art. The mating portion 18, which is preferably made of plastic material, when mated and then securely fixed to the attachment portion 12, attaches the tracking device 20 to the TMS coil device 10 in a precise and predetermined manner.

The plurality of infrared reflective elements 22 can also be capable of reflecting waves having wavelengths other than in the infrared spectrum. In an embodiment, all of the elements 22 are of the same or similar design and are primarily capable of reflecting electromechanical waves in the infrared spectrum. Alternatively, some or all of the elements 22 can be capable of reflecting a broader or a different spectrum of light. Some or all of the elements 22 can reflect waves from a portion or all of the visual spectrum of light. This can be in addition to, or in place of, waves from the infrared spectrum. Additionally, some or all of the elements 22 can reflect a portion or all of the ultraviolet range of electromechanical waves. Similarly, this can be in addition to, or in place of waves form other spectrums. The elements 22 which make up the tracking device 20 can all be uniform or some can be for primarily reflecting, or only capable of reflecting, one set of electromechanical wavelengths and others for primarily reflecting, or capable of reflecting, one or more deferent sets of electromechanical wavelengths. For example, in FIG. 1, the three reflective elements 22 of each set of elements can be for reflecting infrared waves and there can be an additional reflective element (not shown) located within or near the existing set which is capable of reflecting visual light.

Figure 2:
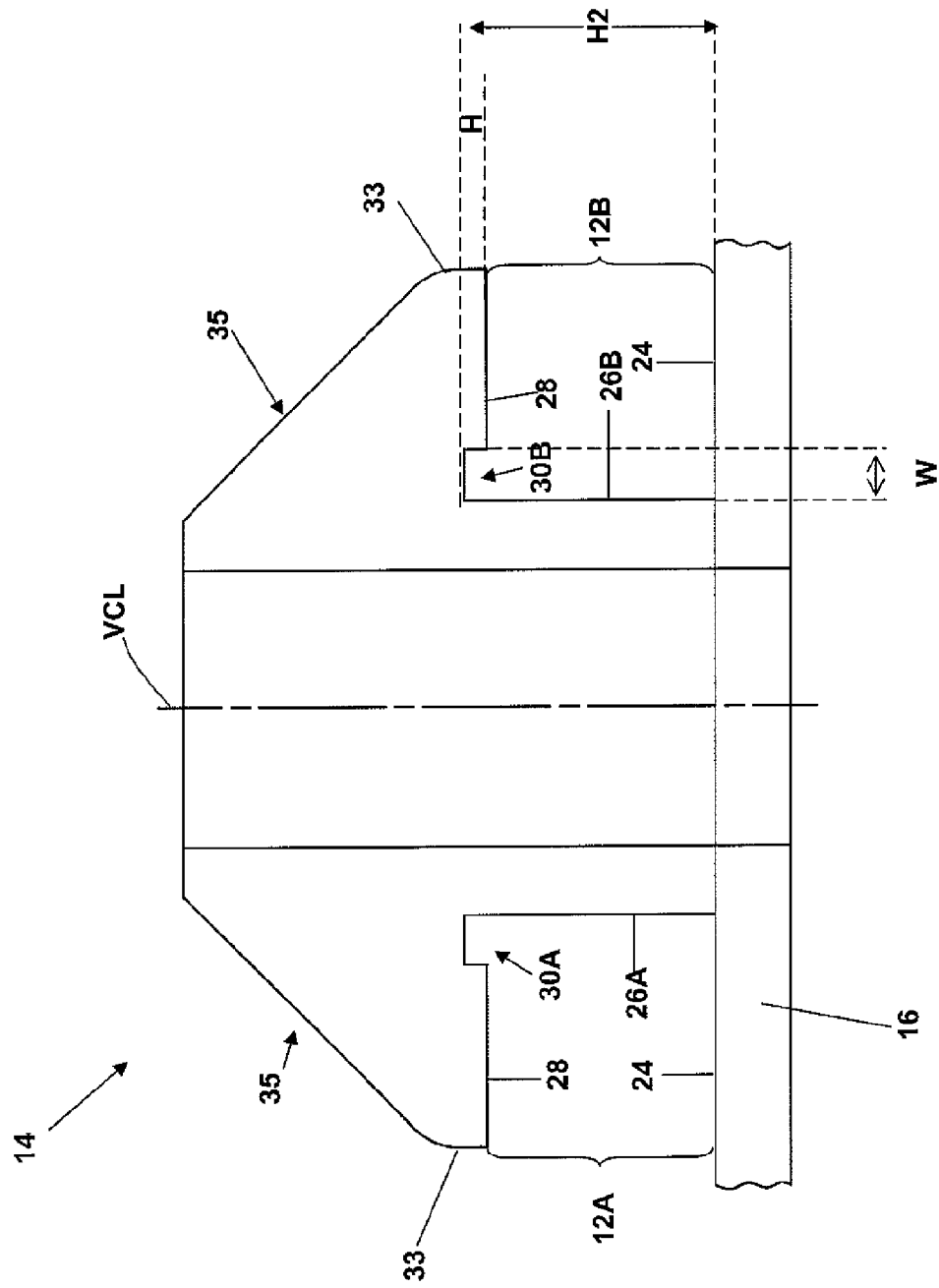
FIG. 2 is a cross-sectional view of a portion of the casing of the TMS coil device of FIG. 1 taken along line 2-2.
Figure 3:
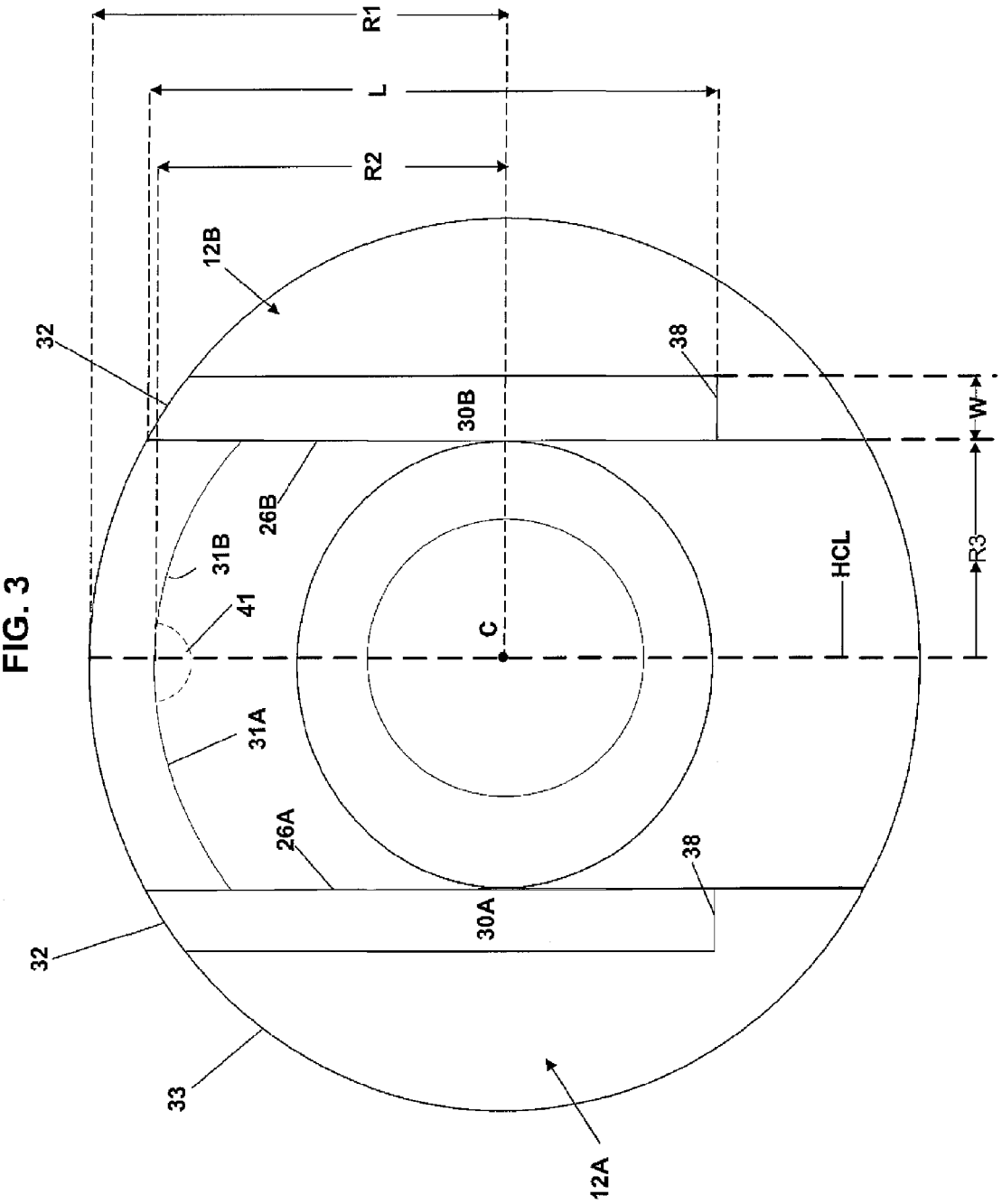
FIG. 3 is a cross-sectional view of the casing of the TMS coil device of FIG. 1 taken along line 3-3.

FIG. 2 shows a cross-sectional view of the casing 14 of the TMS coil device 10 taken along line 2-2 in FIG. 1. Referring to FIGS. 1 and 2, the attachment portion 12 defines two identical receiving regions 12A and 12B disposed symmetrically about vertical center line VCL in the casing 14. Also referring to FIG. 3, which is a view of the casing 14 taken along line 3-3 in FIG. 1, the receiving regions 12A, 12B are disposed symmetrically about horizontal center line HCL in the casing 14. Referring to FIGS. 1, 2 and 3, the attachment portion 12 includes a top surface 28 and lateral surfaces 26A, 26B extending between the top outer surface 24 of the bottom portion 16 and the top surface 28, an arcuate surface 31A extending between the center line HCL and the surface 26A and an arcuate surface 31B extending between the center line HCL and the surface 26B. The casing 14 includes a circumferential surface 33 a radial distance R1 from a center C of the attachment portion 12 and a tapered surface 35 extending between the surface 33 and the handle 17. The circumferential surface 33 circumscribes the top surface 28.

Referring to FIG. 3, each of the arcuate surfaces 31A, 31B of the attachment portion 12 is a radial distance R2 from the center C, where R2 is less than R1 and the difference between R1 and R2 is about 10 mm. In addition, each of the walls 26A, 26B is a radial distance R3 from the center C, where R3 is less than R2.

The region 12A is defined by the arcuate surface 31A, the lateral surface 26A, the portion of the surface 28 extending away from the surface 26A and extending radially away from the surface 31A, and the portion of the surface 24 opposing the portion of the surface 28 extending away from the surface 26A and extending radially away from the surface 31A. The region 12B is defined by the arcuate surface 31B, the lateral surface 26B, the portion of the surface 28 extending away from the surface 26B and extending radially away from the surface 31B, and the portion of the surface 24 opposing the portion of the surface 28 extending away from the surface 26B and extending radially away from the surface 31B. The surface 28 includes substantially rectangularly shaped notches 30A, 30B defined by a portion of the surfaces 26A, 26B, respectively, having a height H and a portion of the surface 28 having a maximum width W. The distance between the surface 28 within the notches 30 and the opposing surface 24 is H2. The outer surface 33 defines one end of the notches 30 and a wall surface 38 extending a distance H away from the surface 28 toward the surface 24 defines the other end of the notches 30. Circumferential surface portion 32 of the surface 33 defines the maximum width W of the notch portion 30. The notches 30 extend a maximum length L between the wall 38 and the opposing end at the outer surface 33. In addition, referring to FIG. 3, an aperture 41 shown in phantom is defined in the surfaces 31A, 31B symmetrically about the HCL line center and approximately intermediate the surfaces 28 and 24.

Referring to FIG. 1, the mating portion 18 of the tracking device 20 has a shape and size complementary to the shape and size of the regions 12A, 12B defined by the attachment portion 12. The mating portion 18 includes rails 40A and 40B having the same shape and spacing from each other as the notches 30A, 30B. Further, the mating portion 18 includes an arcuate portion 47 complementary to the arcuate surfaces 31A, 31B and defining an aperture 49. The aperture 49 extends through the arcuate portion 47 and is positioned on the mating portion 18 so that the aperture 49 would be aligned with the aperture 41 when the mating portion 18 is matingly received within the receiving regions 12A, 12B of the attachment portion 12.

In order to attach the tracking device 20 to the TMS coil device 10, the attachment portion 18 is moved toward and aligned with the mating portion 18 of the tracking device 20, such that the rails 40A, 40B are aligned with the notches 30A, 30B. The rails 40A, 40B are then inserted into and slid along the notches 30A, 30B until ends 45A, 45B of the rails 40A, 40B abut against the wall surface 38 of the notches 30A, 30B, respectively. After the rails 40A, 40B are completely inserted into the notches 30A, 30B, the attachment portion 12 is precisely mated with the mating portion 18 and a screw (not shown) is threaded through the aperture 49 and then the aperture 41 to fix the attachment portion 12 in a mated condition with the mating portion 18. When the attachment and mating portion 12, 18 are in the mated condition, the tracking device 20, including the elements 22, are at a predetermined location and orientation in relation to the bottom portion 16 of the casing 14 and, in particular, the coil windings contained in the casing 14.

While the tracking device 20 is shown as a single device having a plurality of sets of reflective elements 22, there can be multiple tracking devices each having one or more sets of reflective elements 22. In one example, the tracking device 20 of FIG. 1 can be separated in to two, for example by removing the piece 47. The right and left pieces of the tracking device can be attached to the casing of the TMS coil device in the same or similar manner as described with respect to the single tracing device. Additionally, the tracking device can be further separated in to more than two separate sections, preferably each having at least one set of reflective elements 22. Each of the more than one tracking devices can be located at similar locations on the TMS coil device, e.g. in the positions shown in FIG. 1, or in substantially different locations from each other, e.g. one or more of the tracking devices is located above or on the handle 17 and one or more of the tracking devices is located in the indicated positions of FIG. 1. However, regardless of the number of tracking devices that are, or are capable of being attached to the TMS coil device at any given time, each of the tracking devices should be attached in a precise and repeatable manner as described with respect to the whole tracking device 20. In an embodiment where there is more than one tracking device, the type and/or arrangement of reflective elements 22 can be the same or different for each tracking devices.

In a preferred embodiment, precision mating of the tracking device 20 to the TMS coil device 10, in other words, the tracking device 20 is at a predetermined location and orientation in relation to the casing 14, is achieved without the need of external tools. For example, the portions 12 and 18, once mated to each other, do not move relative to each other based on friction. Alternatively, the apertures 41 and 49 include, for example, magnets of opposite polarity that fixedly secure the attachment portion 12 to the mating portion 18. The magnets are of sufficient strength to maintain the portions 12 and 18 mated to each other under ordinary use of the TMS coil device 10, while also allowing the user to remove the tracking device 20 from the TMS coil 10 when desired by pulling the tracking device 20 away from the TMS coil 10. In a further embodiment, a hand operated C-clamp (not shown) can be applied around the portions 18 and 20 when in the mating condition, so as to fixedly secure the portions 18 and 20 to each other.

In a preferred embodiment, the geometrically complementary configurations of the attachment portion 12 and the matching portion 18 advantageously provide that the actual location of the tracking device 20 in relation to the casing 14 is typically at most no more than about 3 mm, preferably no more than about 1 mm, away from the expected location of the tracking device 20 in relation to the casing 14. In a further preferred embodiment, the portions 12 and 18 are constructed from materials, such as, for example, plastic, that do not readily wear away when repeatedly rubbed against each other.

It is to be understood that the precision mating of the casing 14 of the TMS coil device 10 to the tracking device 20 illustrated in FIGS. 1-3 is exemplary, and that any suitable structure for coupling the tracking device 20 to the easing 14 available in the art, such as, for example, snap-on and resilient coupling components, for establishing a precision mating between the tracking device 20 and the TMS coil 10, may be implemented to provide that the tracking device 20 is readily fixedly attachable to and detachable from the casing 14, and when the tracking device 20 is attached and fixed to the casing 14, the tracking device 20 is in a predetermined location and orientation in relation to the casing 14.

Furthermore, the precision mating of the casing 14 of the TMS coil device 10 to the tracking device 20 illustrated in FIGS. 1-3 can be realized at different locations on the TMS coil device. In the example of FIGS. 1-3, the tracking device 20 is attached to the casing 14 below the handle 17. However, the tracking device 20 can be attached in the same or similar manner as those described above at a location on, above, or around the handle 17. Reasons for altering the placement of the tracking device 20 to alternative positions on the TMS coil device 10 can be for improved weighting of the overall device or to account for ergonomical considerations. Similarly, the tracking device can be attached to other portions of the TMS coil device 10.

Thus, during use of the tracking device 20 in conjunction with the TMS coil device 10, and also for maintenance, the tracking device 20 is easily detached from and attached to the casing 14, by uncoupling and coupling the mating portion 16 from and to the attachment portion 14, respectively, without affecting the location and orientation of the tracking device 20 in relation to the casing 14 when the tracking device 20 is attached to the attachment portion 12. As a result, the location and orientation of the tracking device 20 with respect to coil windings (not shown) contained within the bottom portion 16 of the casing 14 is the same each time that the tracking device 20 is attached to the TMS coil device 10. Consequently, where the location and orientation of the coil windings within a casing of a TMS coil device is known in advance, such as where the coil windings are in a casing of the type described in the "TMS Coil Device Manufacture patent application", the location and orientation of the coil windings within the casing in relation to the tracking device 20 that can be attached to the TMS coil device 10 also is accurately known in advance and, therefore, can be used to perform NBS without performing a calibration of the tracking device 20 each time that the tracking device 20 is attached to the TMS coil device 10, or at some interval following continued use of the TMS coil device 10 with the attached tracking device 20.

Advantageously, the construction of the attachment portion and mating portion provide that the location and orientation of the tracking device attached to the TMS coil device with respect to the coil windings in the casing of the TMS coil device remains unchanged during repeated attachment and removal of the tracking device to and from the TMS coil device. Thus, tracking device location and orientation information, once initially determined at the manufacturer or in an initial calibration, can be relied upon for future uses of the TMS coil device with the tracking device attached thereto. The invariability of the location and orientation of the attachment portion in relation to the coil windings, thus, provides for improved accuracy when the TMS coil device is used to perform NBS.

Figure 4:
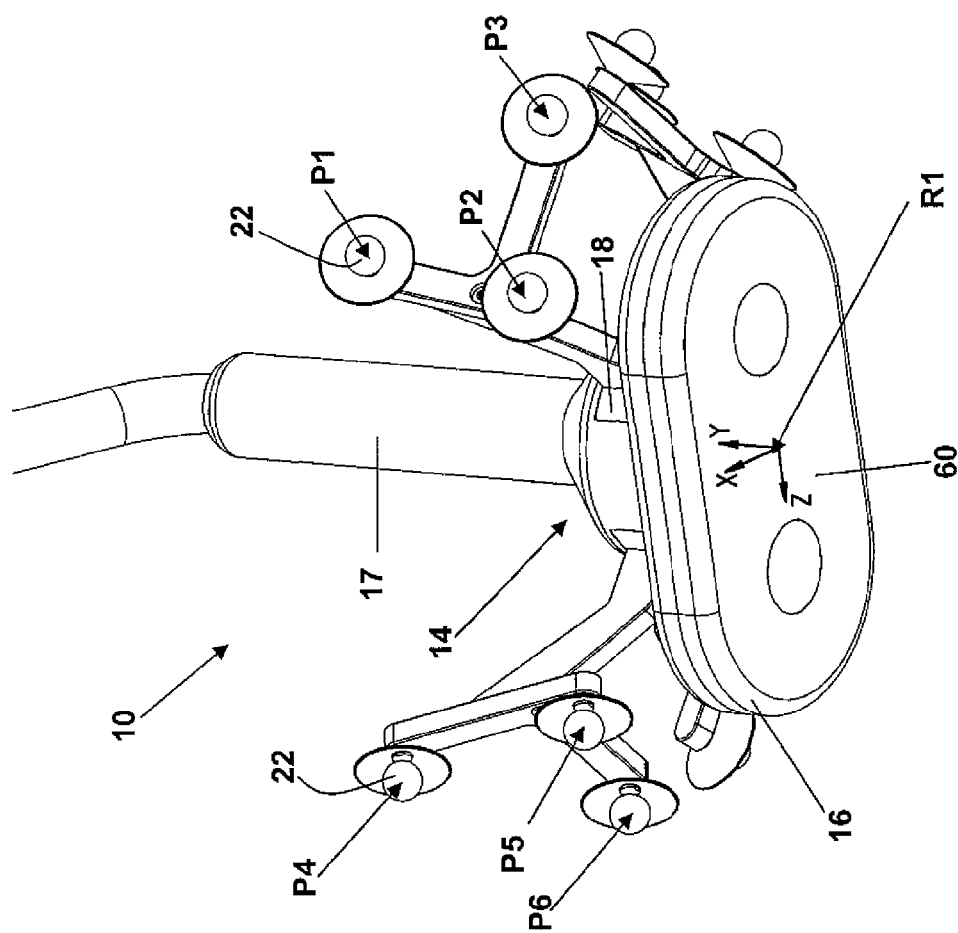
FIG. 4 is a bottom, perspective view of the TMS coil device of FIG. 1 with the tracking device attached to the TMS coil device, in accordance with the present invention.

FIG. 4 shows a perspective, bottom view of the TMS coil device 10 with the tracking device 20 attached in a predetermined location and orientation in relation to the casing 14. Referring to FIG. 4, the bottom portion 16 of the casing 14 includes a bottom surface 60 which, during operation of the TMS coil device 10, is placed adjacent or in contact with a subject's head. In accordance with the present embodiment, the bottom surface 60 includes reflective material at one or more predetermined locations, for example, at a reference point R1 located at the center of the bottom surface 60. It is to be understood that a reference point also may be included elsewhere on the outer surface of the casing 14, or on the outer surface of other portions of the TMS coil device 10.

Based on information representative of the location of the reference point(s) on the casing 14, the accuracy of the location and orientation of the tracking device 20 in relation to the casing 14, when the tracking device 20 is attached to the TMS coil device, can be determined, for example, during production of the TMS coil device or in the field. Information representative of the location of the reference point(s) on the casing 14 may be provided with the TMS coil device, for example, with the sales literature accompanying the TMS coil device. The same, conventional tracking system used to detect the position of the reflective elements 22 of the tracking device 20, when attached to the TMS coil device 10, also detects the position of the reference point. The accuracy of the attachment of the tracking device 20 to the TMS coil device 10, in other words, the difference between the expected and actual location and orientation of the tracking device 20 in relation to the TMS coil device 10, is determined by using the reference points, for example, to create a frame of reference.

Referring to FIG. 4, the tracking device 20 preferably includes sets of three points P1-P3 or P4-P6, which correspond to sets of three reflective elements 22 and are used to form a reference coordinate frame for the TMS coil device 10, for example, where the origin is at the point R1 and the coordinate axes are as shown in FIG. 4. Standard measurement techniques and software tools, as well known in the art, can be used to determine the coordinate frames necessary to check the accuracy of the placement of the tracking device 20 in relation to the TMS coil device 10 using the reference points and, thus, provide that the TMS coil device 10, in combination with the attached tracking device 20, can be used to perform NBS with a desired level of accuracy.

In addition to, or in place of, the reflective material at R1 there can also be a physical anomaly which can be used for calibration purposes. In one example, there is a physical depression, e.g. dimple, at a known spot on the TMS coil device. An exemplary location for the depression is R1 on the base of the TMS coil device, although other locations on the base, casing or other portion of the TMS coil device can be used. This depression can have a shape and dimensions such that it is capable of being positioned on, or receiving, the end of a calibration tool. One example of a calibration tool is a pen-like extension located at a fixed, known position with respect to the TMS device or the tracking system. When the TMS coil device is positioned with the depression over and preferably in contact with the end of the calibration tool, then known techniques can be used to calibrate the system with the known location of the TMS coil device. In other examples, in place of or in addition to a depression, there can be means for selectively securing the TMS coil device to a calibration tool which secures the TMS coil device either only at a certain location or at a certain location and orientation. Means for such selective securing are such as, but not limited to, a recess for receiving a portion of the calibration tool, a snap mechanism, Velcro, magnate, etc.

In one embodiment, the expected location and orientation of the tracking device 20 in relation to the coil windings in the casing 14, which is known from the manufacturer of the device 20, is compared to the actual location and orientation of the tracking device 20 in relation to the coil windings in the casing 14, which is determined by a conventional infrared tracking system that detects the locations of the reference point and the reference elements 22. The actual and expected locations and orientations are then compared, for example, within a processor of a NBS system, and tracking device calibration data for the TMS coil device 10 with the attached tracking device 20, which is used to perform navigated brain stimulation with the TMS coil device 10 and is based on the expected location and orientation of the tracking device 20 in relation to the casing 14, is suitably adjusted if a variance exists between the expected and the actual locations and orientations.

Although preferred embodiments of the present invention have been described and illustrated, it will be apparent to those skilled in the art that various modifications may be made without departing from the principles of the invention.

The invention claimed is:

1. A method for tracking the location of a coil winding of a transcranial magnetic stimulation induction coil device comprising:
    tracking at least one set of two or more reflective elements of a tracking device which is removably attached in a predetermined and repeatable manner to a casing containing at least one coil winding having a known orientation within the casing, and
    determining a location and orientation of the at least one coil winding based on the tracked reflective elements and their known relation to the at least one coil winding, wherein the transcranial magnetic stimulation induction coil device further comprises an attachment portion corresponding to a mating portion of the tracking device for removably attaching the tracking device to the casing such that, when repeatedly attached, the reflective elements have a known orientation with respect to the known orientation of the coil winding, and
    determining the accuracy of the attachment of the tracking device to the casing by determining the distance between an expected and actual location of a reference point on the tracking device and a reference point on the casing and the difference in orientation of the reference point on the tracking device and the reference point on the casing.

2. A method in accordance with claim 1 further comprising:
    calibrating the tracking of the at least one set of two or more reflective elements of the tracking device by placing the transcranial magnetic stimulation induction coil device in a known location with respect to a reference point on the transcranial magnetic stimulation induction coil device.

3. A method in accordance with claim 1, wherein the tracking device includes a set comprising at least three elements at predetermined fixed locations on the tracking device and in predetermined orientations with respect to each other such that, during use, when the tracking device is removably fixed to the attachment portion, the set comprising at least three elements is at a predetermined location and orientation in relation to the attachment portion and form a reference coordinate frame with the at least one reference point.

4. A method in accordance with claim 3, wherein the elements of the tracking device and the at least one reference point are reflective.

5. A method in accordance with claim 1, wherein the at least one reference point at the fixed location on the transcranial magnetic stimulation induction coil device includes an indentation on a surface of the casing.

6. A method in accordance with claim 5, further comprising positioning the indentation over or in contact with the end of a calibration tool, and calibrating a transcranial magnetic stimulation system based on the known location of the transcranial magnetic stimulation induction coil device.

7. A method in accordance with claim 1, wherein the at least one reference point at the fixed location on the transcranial magnetic stimulation induction coil device includes a means for selectively securing the transcranial magnetic stimulation coil device to a calibration tool which secures the transcranial magnetic stimulation coil device at a predetermined location and/or orientation.

8. A method in accordance with claim 1, wherein an expected location and orientation of the tracking device in relation to the coil windings in the casing is known from the manufacturer of the device.

9. A method in accordance with claim 8, wherein the expected location and orientation of the tracking device is compared to the determined location and orientation of the tracking device in relation to the coil windings in the casing.

10. A method in accordance with claim 9, further comprising adjusting tracking device calibration data for the transcranial magnetic stimulation coil device if a variance exists between the expected and determined locations and orientations.

11. A method in accordance with claim 10, wherein the comparison of the expected and determined locations is carried out within a processor of a navigated brain stimulation system.

12. A method in accordance with claim 9, wherein the comparison of the expected and determined locations is carried out within a processor of a navigated brain stimulation system.

* * * * *